United States Patent
Scully et al.

(10) Patent No.: US 10,981,869 B2
(45) Date of Patent: Apr. 20, 2021

(54) DIINDOLE COMPOUNDS USEFUL IN TREATMENT OF NERVOUS SYSTEM DISORDERS

(71) Applicant: Rhode Island Board of Education, State of Rhode Island and Providence Plantations, Providence, RI (US)

(72) Inventors: Kyle Robert Scully, Wakefield, RI (US); Roberta S. King, Narragansett, RI (US); David R. Worthen, Wakefield, RI (US)

(73) Assignee: Rhode Island Board of Education, Providence, RI (US)

( * ) Notice: Subject to any disclaimer, the term of this patent is extended or adjusted under 35 U.S.C. 154(b) by 0 days.

(21) Appl. No.: 16/600,269

(22) Filed: Oct. 11, 2019

(65) Prior Publication Data
US 2020/0095200 A1    Mar. 26, 2020

Related U.S. Application Data

(63) Continuation of application No. 15/611,775, filed on Jun. 1, 2017, now Pat. No. 10,487,055.

(60) Provisional application No. 62/343,887, filed on Jun. 1, 2016.

(51) Int. Cl.
| | |
|---|---|
| *C07D 209/56* | (2006.01) |
| *C07D 209/04* | (2006.01) |
| *C07D 495/18* | (2006.01) |
| *C07D 487/18* | (2006.01) |
| *A61K 31/404* | (2006.01) |
| *A61K 45/06* | (2006.01) |

(52) U.S. Cl.
CPC .......... *C07D 209/56* (2013.01); *A61K 31/404* (2013.01); *A61K 45/06* (2013.01); *C07D 209/04* (2013.01); *C07D 487/18* (2013.01); *C07D 495/18* (2013.01); *A61K 2300/00* (2013.01)

(58) Field of Classification Search
CPC .. C07D 209/56; C07D 209/04; C07D 487/18; C07D 495/18; A61K 31/404; A61K 45/06; A61K 2300/00
USPC .......................................................... 514/410
See application file for complete search history.

(56) References Cited

U.S. PATENT DOCUMENTS 10,487,055 B2 * 11/2019 Scully ................. C07D 209/56
2003/0203959 A1 * 10/2003 Rauer ................. A61K 31/404
                                                              514/414

OTHER PUBLICATIONS

Fukuda et al., The Novel Cyclopropapyrroloindole(CPI) Bisalkylators Bearing Methoxycarbonyl and Trifluoromethyl Groups, 1998, Bioorganic & Medicinal Chemistry Letters, 8, 1387-1390 (Year: 1998).*
Reddy et al., Copper oxide nanoparticles catalyzed synthesis of aryl sulfides via cascade reaction of aryl halides with thiourea, 2011, Tetrahedron Letters, 52, 2679-2682 (Year: 2011).*

* cited by examiner

*Primary Examiner* — Kristin A Vajda
(74) *Attorney, Agent, or Firm* — Milstein Zhang & Wu LLC; Duan Wu, Esq.

(57) ABSTRACT

The invention provides bridged diindole compounds, related pharmaceutical compositions and methods of use thereof, for the prevention, palliation and/or treatment of nervous system disorders.

12 Claims, 5 Drawing Sheets

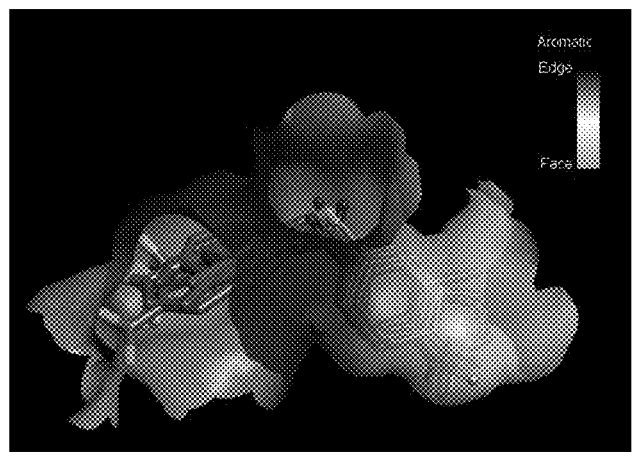
FIG. 3
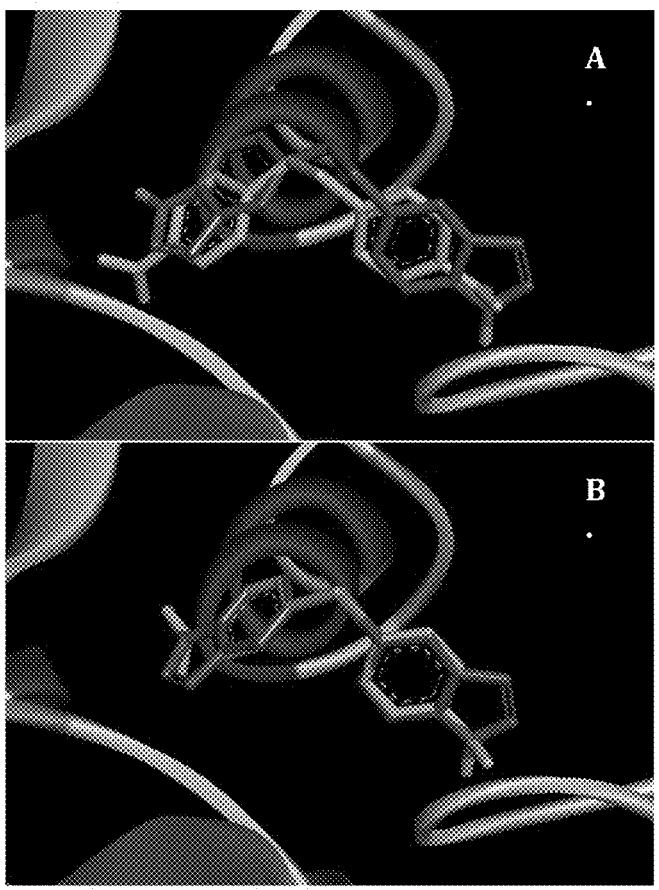
FIG. 4A
FIG. 4B

DIINDOLE COMPOUNDS USEFUL IN TREATMENT OF NERVOUS SYSTEM DISORDERS

CROSS-REFERENCE TO RELATED APPLICATIONS

This application is a continuation application of, and claims priority of and the benefit of, co-pending U.S. patent application Ser. No. 15/611,775, which in turn, claims priority to and the benefit of U.S. provisional patent application Ser. No. 62/343,887, filed on Jun. 1, 2016, which applications are incorporated herein by reference in entirety.

FIELD OF THE INVENTION

The present invention relates to bridged diindole compounds and pharmaceutical compositions and methods of use thereof, as antagonists and partial antagonists at N-methyl-D-aspartate (NMDAR) and at its subunit isoforms, including the NR2A and NR2B subunits, for the prevention, palliation and/or treatment of nervous system disorders or conditions and for the induction of anesthesia, in humans and in animals. Such disorders or conditions include epilepsies, seizures, conduction disturbances and electroconvulsive disorders, pain, fibromyalgia, affective disorders such as bipolar disorder and depression, autism, schizophrenia, Parkinson's disease, Alzheimer's disease, attention deficit disorder, attention deficit hyperactivity disorder, and neurodegeneration of all types, manifestations and origins.

BACKGROUND OF THE INVENTION

Learning and memory, nerve development, Alzheimer's disease, epilepsy, seizures and other electroconvulsive disorders, pain, fibromyalgia, schizophrenia and psychosis, depression and other affective disorders, autism, Parkinson's disease, attention deficit disorder, attention deficit hyperactivity disorder, anesthesia, and neurodegeneration have all been linked to the activity and regulation of the N-methyl-D-aspartate receptor (NMDAR; 1,2). The NMDAR, a nonselective ion channel present on many types of nerve cells, regulates and modifies nerve growth and is directly linked to signaling and nerve activity in the brain. The development of NMDAR modulators, including NMDAR antagonists and partial NMDAR antagonists, as new diagnostic agents and new therapeutic drugs, is a promising area of research.

A number of bridged diindoles that are structurally distinct from compounds known to modify NMDAR activity, as well as from known therapeutic drugs, have been identified as potential NMDAR ligands, partial NMDAR antagonists, NMDAR antagonists, and modulators of NMDAR activity. Computer-based (in silico) modeling studies that assess the affinity and specificity of the chemical interactions between small molecules and large biological molecules, such as the NMDAR, reveal that these novel compounds interact with NMDAR at specific receptor binding sites in unique ways not previously reported in the literature. Studies reveal that these compounds likely act as NMDAR antagonists or partial NMDAR antagonists. This includes activity as antagonists at one or more NMDAR NR2 isoform receptor sites, including NMDAR NR2A and NR2B.

Preliminary in silico modeling data indicate the existence of multiple NMDAR binding sites for these compounds, suggesting that they could be useful for regulating multiple nervous system and brain functions and diseases. In silico modeling experiments using computer programs such as Discovery Studio and AutoDock 4 for modeling interactions of the compounds with crystal structure models of the NMDAR reveal that these compounds bind specifically and with high affinity to sites on the NMDAR including subunit NR2 isoforms, such as NMDAR NR2A and NR2B, at sites that include the entrance to a cavity that also contains the activating agonist (glutamate) binding site.

Bridged diindole and bis-diindole compounds and their derivatives, both synthetic and naturally occurring, have been reported. Most of these have physical-chemical properties and commercial utility completely unrelated to biological or pharmacological activity, as evidenced by their use as combustion modifiers, polymerization initiators and promoters, electrical conductors, and glass materials (3,4). A number of bridged diindole compounds, including those with a methylene, a ketone, a sulfide, and a sulfone as bridging moieties, do have biological activity. However, their chemical structures are clearly distinct from those contemplated in the present invention, as are their purported biological activities, which are completely distinct from the NMDAR antagonist activity and nervous system effects contemplated by the compounds revealed in the present invention. These include: DNA-binding and alkylating agents proposed for cancer treatment (5,6); antibiotics and antibacterial agents (7-9); and biological effects related to the serotonin (5-HT) receptor (10,11).

A number of drugs that modulate NMDAR activity, including NMDAR antagonists, are available or are under development for treating these aforementioned NMDAR-related nervous system pathologies (12). These include: Alzheimer's disease and other memory disorders (13); status epilepticus and other electroconvulsive disorders (14); pain-related disorders (15,16); schizophrenia (17); autism (18); and depression and other mood disorders (19-21), including the effects of NMDAR activity modulation on depression and mood disorders by molecular modeling methods (22).

Given the enormous therapeutic potential of NMDAR antagonists as palliatives and treatments for nervous system disorders, several published patents and patent applications teach the synthesis and use of novel NMDAR modulators, including NMDAR antagonists, as therapeutic agents for nervous system disorders. Although completely unrelated chemically to the compounds that are the subject matter of the present invention, these patents and applications describe specific NMDAR antagonists, discrete NMDAR subunit antagonists, and the proposed therapeutic activity of NMDAR ligands for nervous system pathologies (23-27).

However, many of these agents have a number of shortcomings. For instance, the agents may be poorly soluble in aqueous and biological fluids or may be extremely hygroscopic, thereby complicating their formulation and delivery to patients and to their active sites. Moreover, the agents may be chemically and/or physically unstable. They may be inherently toxic, or they may undergo conversion to toxic degradants in storage or when metabolized. Many of these agents are not absorbed by the oral route, thus requiring more expensive and invasive modes of administration, such as needle injection. Of even greater importance is that patients may become refractory to these drugs over time. Many patients require multi-drug therapy in order to achieve a desired clinical effect. In addition, many current NMDAR-modulating agents cause unwanted side effects, neurotoxicities, and drug interactions.

As an example, the drug treatments currently available for one subset of the aforementioned, NMDA-influenced nervous system pathologies, epilepsy and other electroconvulsive disorders, exemplify many of these therapeutic drug limitations. These include refractory loss of drug effect, the need for multiple drug therapy, undesirable side effects, drug and dietary interactions, and a decrease in patient quality of life (28). As novel NMDAR-modulating compounds, such as those that are included in the subject matter of the present invention, are identified and developed, the clinician will have expanded pharmaceutical options when designing an effective treatment protocol for each patient. This possibility clearly underscores the utility of the present invention.

The need for novel compounds that interact with the NMDAR as therapeutic agents is further underscored by the fact that many NMDA-modulating compounds, such as anti-epilepsy compounds, are effective in the treatment of other central nervous system disorders, including bipolar disorder, fibromyalgia, migraine prophylaxis, neuropathic pain, and chronic pain, alone or in combination with other biologically active agents. These novel compounds would ideally interact chemically with the NMDAR in a manner that is distinct from current NMDAR-modulating agents and ligands. They might also interact with one or more sites in the central nervous system that are distinct from the purported sites and modes of action of current agents.

SUMMARY OF THE INVENTION

After in silico investigation, it has been discovered bridged diindole compounds of the type represented in Formula I (below) avidly interact with and bind to the NMDAR, and to its subunits, including the NR2A and NR2B subunits, and likely act as antagonists or partial antagonists to NMDAR. As NMDAR antagonists and partial antagonists, these compounds, whose pharmacological activity on the central and peripheral nervous systems has never been reported, are useful as preventative, palliative, and therapeutic agents for nervous system disorders and conditions, including conditions such as Alzheimer's disease, epilepsy, seizures and other electroconvulsive disorders, pain, fibromyalgia, schizophrenia and psychosis, depression and other affective disorders, autism, Parkinson's disease, attention deficit disorder, attention deficit hyperactivity disorder, and neurodegeneration. They are also useful as anesthetic agents or anesthetic adjuncts.

In one aspect, the invention relates to a compound having a structural formula as follows:

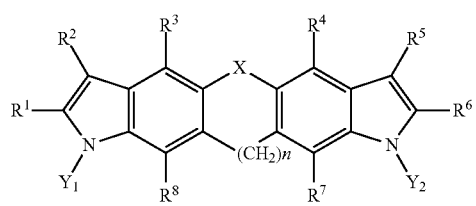

(I)

where, X is selected from the group consisting of —O—, —S—, —N(H)—, —Se—, —Si—, —CH$_2$—CH$_2$—, —CH$_2$—CH$_2$—CH$_2$—, —CH$_2$—CH$_2$—CH$_2$—CH$_2$—, (cis)-CH=CH—, (trans)-CH=CH—, —CH=CH—CH$_2$—, —CH$_2$—CH=CH—, —N=N—, —N=CH—, —CH=N—, —C(S)—, —N(H)S(O)—, —N(H)SO$_2$—, —N(H)O—, —N(H)S—, —S(O)—, —SO$_2$—, —PO$_4$—, —C(O)—, —CH$_2$—, —CF$_2$—, —C(CH$_3$)$_2$—, and a covalent bond;

Y$_1$ and Y$_2$ are each independently selected from the group consisting of hydrogen, deuterium, and tritium;

n is an integer from 0 to 6; and

R$^1$, R$^2$, R$^3$, R$^4$, R$^5$, R$^6$, R$^7$, and R$^8$ are each independently selected from the group consisting of hydrogen, hydroxyl, carboxyl, amino, aminoalkyl, nitro, hydroxymethyl, hydroxyalkyl, acetate, propionate, butyrate, thiol, thioalkyl, nitrile, a halogen, trifluoromethyl, methoxy, ethoxy, phenyl, guanidino, amidino, amide, alkylamide, sulfate, phosphate, imidazole, thiazole, a substituted or unsubstituted C$_{1-10}$ alkyl, a substituted or unsubstituted branched C$_{3-10}$ alkyl, a substituted or unsubstituted C$_{3-10}$ cycloalkyl, a substituted or unsubstituted arylalkyl, and a covalent bond.

In preferred embodiments, the compound of the invention comprises a thiodiindole or an ethylenediindole. In a feature, the compound effectively inhibits a function of a N-methyl-D-aspartate receptor (NMDAR) in an animal, such as an mammal including *Homo sapiens*. The compound, in some embodiments, binds at least one of NMDAR's subunit isoforms, the NR2A and NR2B subunits.

In a further aspect, the invention relates to a pharmaceutical composition, comprising the compound of the invention as described herein, and a pharmaceutically acceptable excipient, carrier, or diluent. When referring to the compound of the invention, it is intended to include all resolved enantiomers, diastereomers, tautomers, salts, solvates and polymorphic forms of Formula I. The pharmaceutical composition of the invention can be in an admixture, dosage form, delivery system, food, or vehicle with biologically and pharmaceutically acceptable carriers, adjuvants, excipients, and diluents.

According to a further aspect of the invention, a method is provided to treat (including to prevent and/or ameliorate) a disorder or pathological condition in a subject, which may be a human or an animal patient. The method includes administering to a subject in need thereof a therapeutically effective amount of the pharmaceutical composition of the invention. The disorder or condition includes epilepsies, seizures, conduction disturbances and electroconvulsive disorders, pain (e.g., neuropathic and chromic pains), fibromyalgia, affective disorders such as bipolar disorder and depressive disorders including major depression, depression, dysthymia, cyclothymia, and post-partum depression, autism, schizophrenia, Parkinson's disease, Alzheimer's disease and other dementias, attention deficit disorder, attention deficit hyperactivity disorder, and neurodegeneration of all types, manifestations and origins including post-stroke neurodegeneration and related sequelae.

In a feature, the therapeutically effective amount of the pharmaceutical composition of the invention effectively inhibits a function of the N-methyl-D-aspartate receptor (NMDAR) in the subject. In various embodiments, the therapeutically effective amount is from about 0.1 mg/kg to about 300 mg/kg.

According to yet another aspect of the invention, a method is provided for inducing or augmenting anesthesia. The method includes a step of administering to a subject in need thereof a therapeutically effective amount of the pharmaceutical composition of the invention, alone or in combination with other agents, drugs, foods, supplements, or procedures.

Additional advantages of the present invention will become readily apparent to those skilled in the art from the following detailed description. As will be realized, the invention is capable of other and different embodiments, and its several details are capable of modifications in various obvious respects, all without departing from the present invention.

BRIEF DESCRIPTION OF THE DRAWINGS

FIG. 3 illustrates aromatic characteristics of the model NMDAR NR2A subunit cavity in which the affinity and binding characteristics of bridged diindole and diaminodiphenyl compounds were assessed in silico, according principles of the present invention.

FIGS. 4A and 4B illustrate binding orientations of 4,4'-ethylenedianiline and ethylene diindole in (4A); and 4,4'-thiodianiline and thiodiindole in (4B).

DETAILED DESCRIPTION OF THE INVENTION

I. Definition

Figure 1:
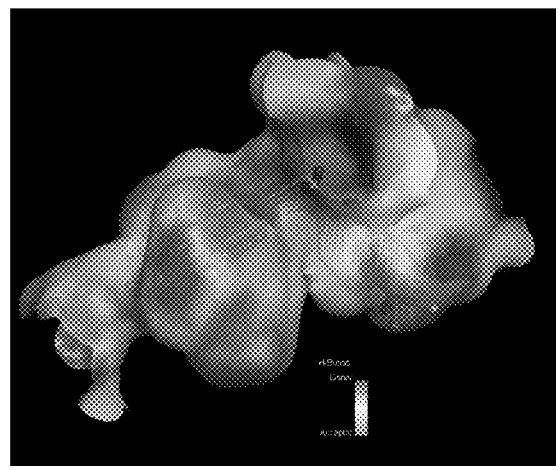
FIG. 1 illustrates hydrogen-bonding characteristics of the NMDAr NR2a subunit cavity into which the model compounds were bound according to the invention.

Unless otherwise noted, technical terms are used according to conventional usage. Definitions of common terms in molecular biology may be found, for example, in Lewin's Genes XII, published by Jones and Bartlett Learning, 2018 (ISBN 1284104494), J. Krebs et al. (eds.) and other similar technical references.

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, terms such as "treating" or "treatment" or "to treat" or "alleviating" or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented.

As used herein, the terms "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refer to a reduction of about 20%, 30%, 40%, 50%, 60%, 70%, 80%, 90% or 95% of the targeted activity. When used in the context of a disorder or disease, the terms refer to success at preventing or significantly delaying the onset of symptoms, alleviating symptoms, or eliminating the disease, condition or disorder.

The term "pharmaceutically acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

II. Description

A series of bridged diindole compounds were identified through in silico modeling studies as interacting avidly and discretely with the N-methyl-D-aspartate receptor (NMDAR), including the NMDAR subunit isotypes NR2A and NR2B, located in the mammalian nervous system, apparently resulting in NMDA receptor antagonism or partial antagonsim. Such an in silico model is often predictive of those compounds that are active in vivo, and those that are inactive in vivo. Structure-activety relationship (SAR) studies have afforded information related to the chemical structural motifs and requirements for in silico binding and likely in vivo activity.

The subject matter of the present invention relates to bridged diindole compounds according to Formula I and their use for the prevention, palliation and/or treatment of seizures, conduction disturbances and electroconvulsive disorders of all types, manifestations and origins, in humans and other mammals, and for pain, affective disorders such as bipolar disorder and depression, autism, schizophrenia, Parkinson's disease, attention deficit disorder, attention deficit hyperactivity disorder, and neurodegeneration of all types, manifestations and origins, and for the induction of anesthesia, in a human or other mammal.

Specifically, the present invention provides pharmaceutical preparations and the uses thereof for the prevention, palliation and/or treatment of the aforementioned nervous system pathologies by administering a pharmaceutically effective amount of a therapeutic compound according to Formula I, as described above.

Embodiments include administering an effective amount of a compound according to Formula I, an analog, derivative, prodrug, or a pharmaceutically accepted salt, complex, solvate, or polymorph thereof, to a mammal in need of treatment or prevention of epilepsy, seizure, or other electroconvulsive disorder.

Embodiments include administering an effective amount of a compound according to Formula I, an analog, derivative, prodrug, or a pharmaceutically accepted salt, complex, solvate, or polymorph thereof, to a mammal in need of treatment or prevention of bipolar disorder.

Embodiments include administering an effective amount of a compound according to Formula I, an analog, derivative, prodrug, or a pharmaceutically accepted salt, complex, solvate, or polymorph thereof, to a mammal in need of treatment or prevention of depressive disorders, including major depression, depression, dysthymia, cyclothymia, and post-partum depression.

Embodiments include administering an effective amount of a compound according to Formula I, an analog, derivative, prodrug, or a pharmaceutically accepted salt, complex, solvate, or polymorph thereof, to a mammal in need of treatment or prevention of neuropathic pain.

Embodiments include administering an effective amount of a compound according to Formula I, an analog, derivative, prodrug, or a pharmaceutically accepted salt, complex, solvate, or polymorph thereof, to a mammal in need of treatment or prevention of chronic pain.

Embodiments include administering an effective amount of a compound according to Formula I, an analog, derivative, prodrug, or a pharmaceutically accepted salt, complex, solvate, or polymorph thereof, to a mammal in need of treatment or prevention of fibromyalgia.

Embodiments include administering an effective amount of a compound according to Formula I, an analog, derivative, prodrug, or a pharmaceutically accepted salt, complex, solvate, or polymorph thereof, to a mammal in need of treatment or prevention of neurodegeneration.

Embodiments include administering an effective amount of a compound according to Formula I, an analog, derivative, prodrug, or a pharmaceutically accepted salt, complex, solvate, or polymorph thereof, to a mammal in need of treatment or prevention of autism.

Embodiments include administering an effective amount of a compound according to Formula I, an analog, derivative, prodrug, or a pharmaceutically accepted salt, complex, solvate, or polymorph thereof, to a mammal in need of treatment or prevention of schizophrenia.

Embodiments include administering an effective amount of a compound according to Formula I, an analog, derivative, prodrug, or a pharmaceutically accepted salt, complex, solvate, or polymorph thereof, to a mammal in need of treatment or prevention of central nervous system damage and related sequelae secondary to stroke.

Embodiments include administering an effective amount of a compound according to Formula I, an analog, derivative, prodrug, or a pharmaceutically accepted salt, complex, solvate, or polymorph thereof, to a mammal in need of treatment or prevention of Parkinson's disease.

Embodiments include administering an effective amount of a compound according to Formula I, an analog, derivative, prodrug, or a pharmaceutically accepted salt, complex, solvate, or polymorph thereof, to a mammal in need of treatment or prevention of an attention deficit disorder.

Embodiments include administering an effective amount of a compound according to Formula I, an analog, derivative, prodrug, or a pharmaceutically accepted salt, complex, solvate, or polymorph thereof, to a mammal, alone or in combination with other agents or procedures, for the induction or maintenance of anesthesia.

It has been discovered that compounds according to Formula I avidly interact with and bind to the NMDAR, and with its subunits and its subunit isoforms, including the NR2A and NR2B subunits, and may act as antagonists and partial antagonists to the NMDAR. As NMDAR antagonists and partial antagonists, these compounds, whose central and peripheral nervous system pharmacological activity has never been reported, are likely to be useful as preventative, palliative, and therapeutic agents for nervous system conditions, including central nervous system conditions, such as Alzheimer's disease, epilepsy, seizures and other electroconvulsive disorders, pain, fibromyalgia, schizophrenia and psychosis, depression and other affective disorders, autism, Parkinson's disease, attention deficit disorder, attention deficit hyperactivity disorder, and neurodegeneration of all types and manifestations irrespective of the origin of the ailment in a subject in need thereof including humans and other mammals. It is contemplated that the inventive compositions can be employed for preventing and/or treating other conduction disturbances of the central nervous system (CNS), and the emotional, cognitive, and motor symptoms resulting there from.

In an embodiment of the present invention, the inventive compositions are administered to a subject in need thereof to prevent or treat those disturbances of the nervous system as mentioned above, of either or both an acute or chronic nature, of unknown origin or secondary to conditions such as, but not limited to: surgery, irradiation, or other manipulation of the brain and/or CNS; alcohol, benzodiazepine, barbiturate or other drug or chemical withdrawal; exposure to exogenous drugs and/or chemicals; acute or chronic injury or trauma; stroke or cerebrovascular accident; fever; meningitis or other CNS inflammation or infection; or electroconvulsive therapy.

In practicing the present invention, the compound having Formula I, or an analog, derivative, prodrug, or a pharmaceutically accepted salt, complex, solvate, or polymorph thereof, is formulated into pharmaceutical compositions.

The compound of Formula I includes all resolved enantiomers, diastereoisomers, tautomers, salts, solvates and polymorphic forms thereof. Such salts include, but are not limited to, the following: inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, benzenesulfonate, and ascorbate; salts with acidic amino acids such as aspartate and glutamate; base addition salts, such as the salts of acidic compounds according to Formula I formed by the addition of inorganic based such as an alkali hydroxide or an amine base. The salts may in some cases be hydrates or solvates with water, acetone, alcohols, and other solvents, and combinations thereof, and mixtures thereof. Salt forms of compounds according to Formula I can be prepared by methods known to those skilled in the art, such as by dissolving, mixing, or co-precipitating the compound and the salt-forming acid or base in a conventional solvent, with or without alcohols or water, and evaporating or precipitating the resulting addition salt, or by spray-drying the components together, or by co-precipitation, or by other known methods.

The compounds of the present invention are useful in pharmaceutical compositions for systemic administration to mammals including humans as a single agent, or as a primary or adjunct agent with any other medication, chemical, drug or non-drug therapy, procedure, or combination thereof.

The aforementioned administration of said compounds according to Formula I is to be employed acutely, or as a single dose, or administered intermittently, or on a regular schedule of unspecified duration, or by continuous infusion of unspecified duration, by an acceptable route of administration including, but not limited to, the oral, buccal, sublingual, intranasal, pulmonary, transdermal, rectal, vaginal, intradermal, intrathecal, intravenous, intramuscular, and/or subcutaneous routes.

These pharmaceutical preparations can be employed in dosage forms such as tablets, capsules, microcapsules, particles, pills, bulk or divided powders, granules, suppositories, sterile and parenteral oral solutions or suspensions, sterile and non-parenteral solutions or suspensions, oral solutions or suspensions, disperse systems such as lotions, creams, ointments, gels, and the like, containing suitable quantities of the active ingredient according to Formula I. Topical application can be in the form of ointments, creams, lotions, jellies, sprays, douches, microneedle patches, and the like. For oral administration either solid or fluid dosage forms can be prepared with the compounds of Formula I.

For example, the compounds can be mixed with conventional ingredients such as dicalcium phosphate, magnesium aluminum silicate, magnesium stearate, calcium sulfate, starch, talc, lactose, acacia, methylcellulose, polyvinylpyrrolidones, celluloses, and chemically and functionally similar materials as pharmaceutical excipients or carriers. A sustained release formulation may optionally be used. Capsules may be formulated by mixing the compound with a pharmaceutical diluent which is inert and loading this mixture into a capsule such as a hard gelatin or hydroxypropylmethylcellulose capsule having the appropriate size. If soft capsules are desired, a solution, dispersion, or slurry of the compound with an acceptable solvent, continuous phase, vegetable oil, other inert oil can be encapsulated by machine into a soft capsule, such as a soft gelatin capsule.

Suspensions, syrups, and elixirs may be used for oral administration of fluid dosage forms. A fluid preparation including oil may be used for oil soluble forms. A vegetable oil, such as corn oil, peanut oil, or safflower oil, for example, together with flavoring agents, sweeteners, and any preservatives produces an acceptable fluid preparation. A surfactant, sweetener and flavor may be added to water to form syrup for fluid dosages. Hydro-alcoholic pharmaceutical preparations may be used that have an acceptable sweetener, such as sugar, saccharine, or a biological sweetener and a flavoring agent in the form of an elixir.

Pharmaceutical compositions for parenteral and suppository administration can also be obtained using techniques standard in the art. Another preferred use of the compounds is in a transdermal parenteral pharmaceutical preparation in a mammal such as a human.

In this case, the active compound or compounds can be present in the reservoir alone or in combination form with pharmaceutical carriers. The pharmaceutical carriers acceptable for the purpose of this invention are the carriers known in the art that do not adversely affect the drug, the host, or the material comprising the drug delivery device or dosage form, or their containers or packaging. Suitable pharmaceutical carriers include: sterile water; saline; dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, and emulsifying agents and the like, with or without a penetration enhancer.

The terms "effective amount," "therapeutic amount," "therapeutic effective amount" or "effective dose" mean the amount sufficient to elicit the desired pharmacological or therapeutic effect, thus resulting in the amelioration, prevention or treatment of the condition or disorder. Thus, when treating an aforementioned nervous system disorder, an effective amount of compound is that amount sufficient to be absorbed into the target tissues, to interact with the pharmacological target peripherally, and to pass across the blood-brain barrier of the subject and interact with relevant receptor sites in the brain of the subject. Prevention of the condition or disorder is manifested by delaying or preventing the onset of the symptoms of the condition or disorder. Treatment of the condition or disorder is manifested by a decrease in the symptoms associated with the condition or disorder, or a reduction in the recurrence of the symptoms of the condition or disorder.

The effective dose can vary, depending upon factors such as the condition of the patient, the severity of the symptoms of the disorder, age, weight, diet, metabolic status, concurrent medications, species, and the manner in which the pharmaceutical composition is administered. Typically, the effective dose of compounds generally requires administering the compound in an amount ranging from about 0.1 to about 500 mg/kg of the subject's weight. In an embodiment of the present invention, a dose of about 0.1 to about 300 mg/kg is administered once, intermittently, or daily, or indefinitely, or until symptoms associated with the condition or disorder cease. Preferably, about 0.05 to 50 mg/kg body weight is administered per day. The required dose may be less when administered parenterally, transdermally, buccally, or rectally as compared to other routes of administration.

EXAMPLES

Example 1

In silico computerized modeling has revealed that examples of the bridged diindole compounds that are part of the subject matter of the present invention interact avidly with the NMDAR and its subunits, and may serve as antagonists or partial antagonists to the NMDAR.

In Silico Ligands

Ligands were created using ChemBio3D Ultra 12. All ligands were drawn using program defaults, and then the energy of each ligand was minimized using the MM2 energy minimization function before being saved in a format suitable for docking in AutoDock4.2.

In Silico NMDA Model

Several crystal structures of NMDAr have been reported in the Protein Data Bank (PDB).

Figure 2:
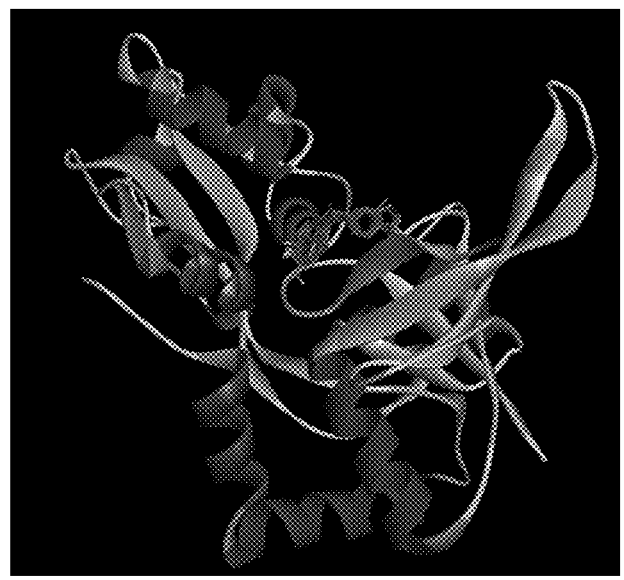
FIG. 2 illustrates overlay of bridged diindole and comparison diaminodiphenyl compounds and derivatives whose orientation and RMS deviation overlap lead to similar binding interactions with the NMDAr NR2A subunit. (The compounds include dapsone, diaminobenzophenone, diaminodiphenyl methane, oxydianiline, diaminodiphenyl sulfide, ethylenedianiline, ethylenediindole, thiodiindole, methylene bis(chloroaniline), and methylene bis(2,6-dimethylaniline).
Figure 5A:
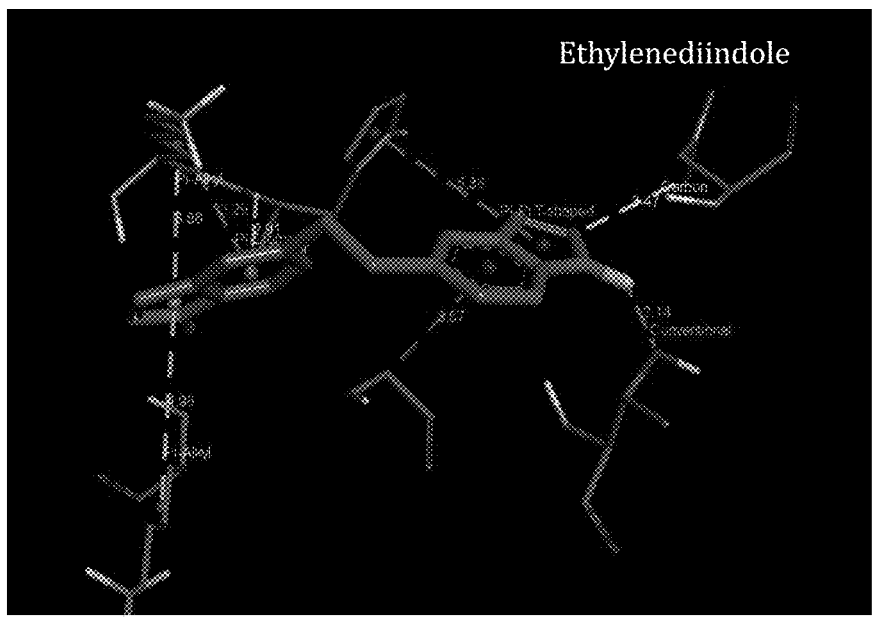
FIGS. 5A and 5B are coordinate maps of the proposed binding interactions of diindole compounds with the NMDAR NR2A subunit: with ethylene diindole in (5A) and thiodiindole in (5B).
Figure 5B:
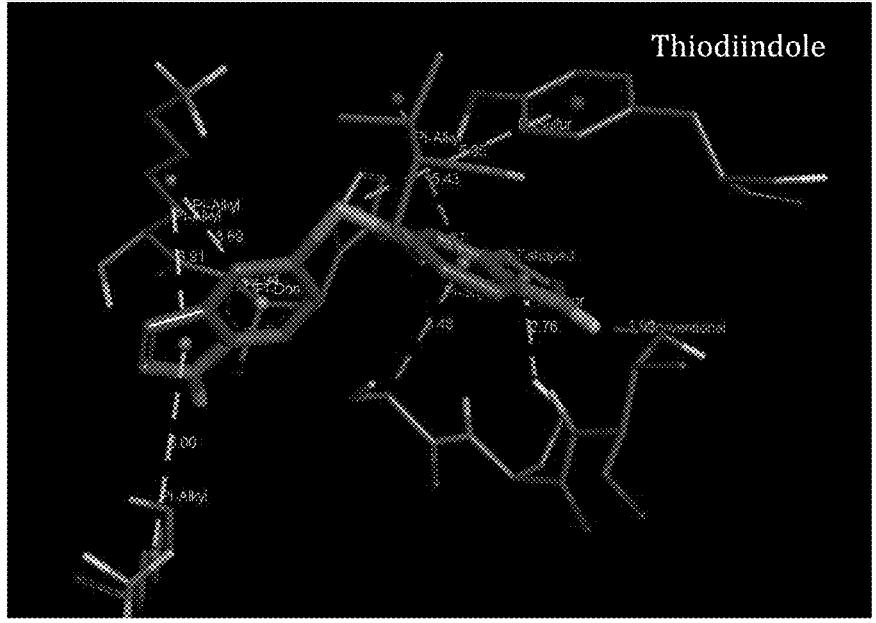
Figure 6A:
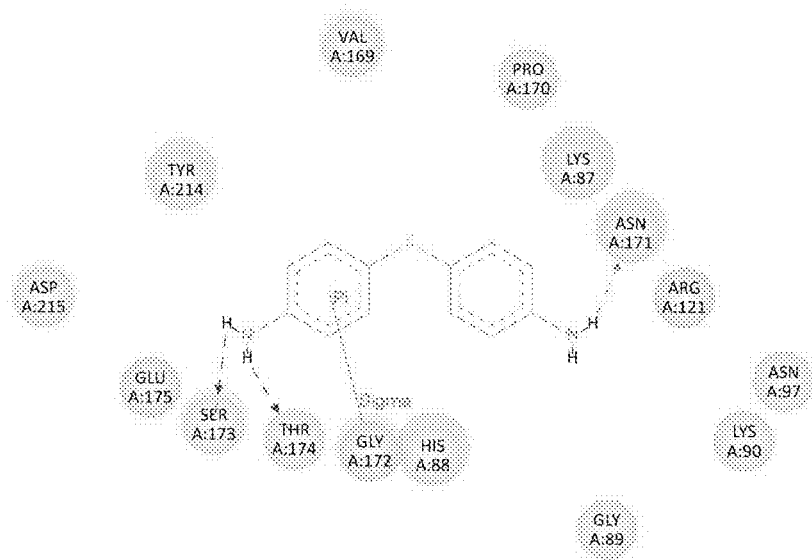
FIGS. 6A-6D show modeled interactions between specific amino acid residues within the NMDAR binding site and: (6A) thiodianiline, (6B) thiodiindole, (6C) ethylene dianiline, and (6D) ethylenediindole.
Figure 6B:
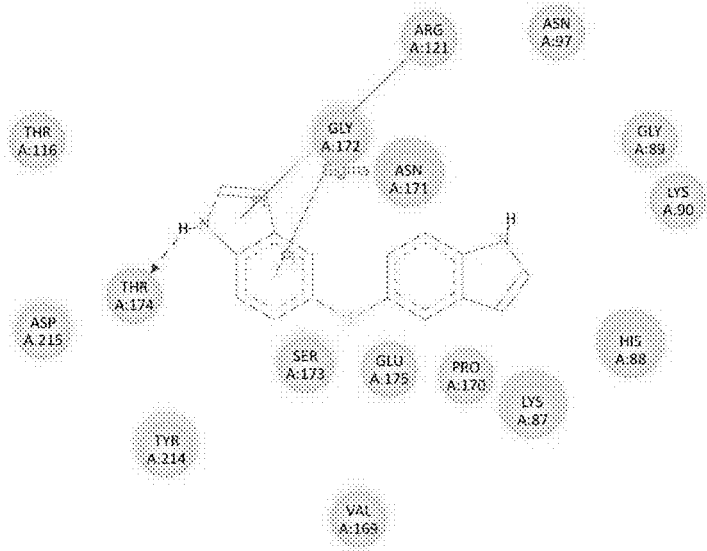
Figure 6C:
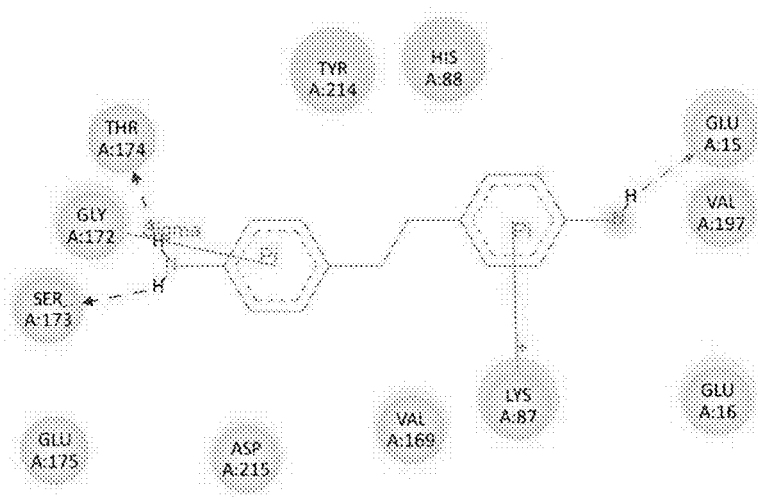
Figure 6D:
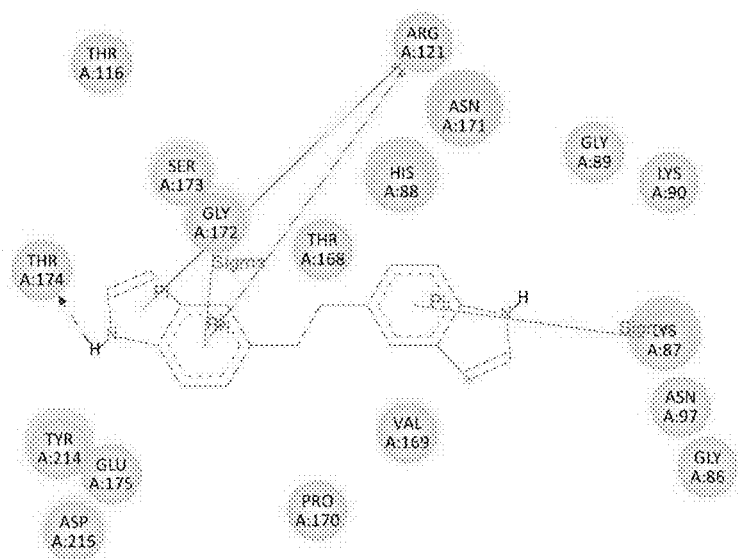

Selection of the crystal structure 2A5S, (Furukawa and Singh, *Nature* (2005) 438: 185-192) from PDB was based on the energy scores and bond angle analysis provided by PDB.org. The structure is composed of 284 amino acids isolated from rat and represents the core ligand binding domain of NMDAR NR2A. The structure was co-crystallized with glutamate and determined to a resolution of 1.7 angstroms using X-ray diffraction. Using Accelrys Discovery Studio 3.1, all amino acid and charge corrections were completed before the removal of the ligand and water molecules. The file was then converted to MOL2, a suitable format for use in AutoDock 4.2. Further analysis of the protein structure, using Discovery Studio 3.1, included determination of the ligand binding site location. A cavity (FIGS. 1 through 3) was characterized and used to define the coordinates of the grid box used in future docking experiments.

In Silico Docking to NMDAR NR2A

Grid Box Selection

The grid box was initially centered on the ligand glutamate and further refined, using the coordinates determined previously in Discovery Studio 3.1, in order to encompass the cavity of the protein in which glutamate binding was characterized. The grid was centered at (21.5, 21.4, 36.1) with dimensions of:

Grid map x-dimension: 22.5 Angstroms
Grid map y-dimension: 22.5 Angstroms
Grid map z-dimension: 24.0 Angstroms The gridbox was overlaid on the water-free ligand-free structure 2A5S produced in Discovery Studio 3.1 and processed using default AutoGrid parameters in AutoDock-Tools 4.2.

AutoDock Parameters

AutoDock parameters were held constant when docking each ligand with the prepared NMDAR NR2A structure 2A5s. Each ligand was docked starting from a computer generated seed site to the protein within the gridbox previously described. Using default Lamarckian Algorithm settings set to default short run in AutoDock 4, the energy was minimized. Optimum binding energy and ligand conformation was then determined and recorded by AutoDock. This process was repeated 256 times for each ligand and the data wwere compiled. The conformations were then grouped based on similar location and orientation with a 2 angstrom deviation to the mean of the population as the grouping criteria.

Modeling Results

Bridged diindole compounds appear to bind to the NMDAR, including NR2 subunits such as the NR2A subunit, in a specific orientation. Hydrogen bonding with THR174 may contribute to their biological and pharmacological effects. In an effort to elucidate the binding interactions of these compounds with NMDAR, the crystal structure of the NR2A subunit of NMDA was examined and the agonist, glutamate, binding site was identified and the binding cavity was characterized. The binding cavity is rich with hydrogen bond donors and acceptors and also possesses the ability to extensively interact with ligands by pi-bonding. The capacity of an NMDAR ligand, such as a bridged diindole, to interact with the receptor and its subunits appears to be dependent in part upon the presence of hydrogen bond-donating amines and pi-stacking aromatic ring systems, separated by a relatively flexible bridging moiety, and in discrete orientations.

Two modelled bridged diindoles, thiodiindole and ethylenediindole, were evaluated in this model. Such compounds retain hydrogen bond donors at the nitrogens, while the large aromatic indole moieties have strong pi-stacking capacity. The binding energy of both thiodiindole, −10.42 kcal/mole, and ethylenediindole, −10.88 kcal/mole, are more favorable than representative diaminodiphenyl compounds, which were also evaluated in tandem with bridged diindoles in order to compare the binding affinities of bridged diindoles with bridged diaminodiphenyls. Both indole derivatives bound in the same orientation as the comparison diaminodiphenyl compounds, and manifested hydrogen bonding with THR 174. Further, the binding affinities of representative bridged diindoles were orders of magnitude higher than diaminodiphenyl comparisons. The computational inhibition constants for diaminodiphenyls which bound in a favorable orientation and hydrogen bonded to THR 174 ranged from 7.38 μM to 517.15 nM. As compared to analogous diaminodiphenyls, the diindole compounds had ca. 100-fold increases in their computational inhibition constants. For example, 4,4'-diaminodiphenyl sulfide had an inhibition constant of 2.54 μM, while the corresponding thiodiindole, had an inhibition constant of 23.01 nM. Likewise, 4,4'-ethylenedianiline had an inhibition constant of 1.19 μM, whereas, with the corresponding ethylenediindole, the inhibition constant was calculated to be 10.54 nM. A summary of these in silico experiments, demonstrating the affinity and binding characteristics of bridged diindoles, and those of bridged diaminodiphenyls as comparisons, with the NMDAR, including its subunits, is presented in the figures and tables.

TABLE 1

Ligand binding energy and root mean squared deviation of the ligand root from a reference point in space within the crystalline structure of NMDAr NR2a subunit.

| Ligand | Binding Energy (Kcal/mole) | RMS |
| --- | --- | --- |
| 4,4'-methylene Bis(chloroaniline) | −8.58 | 41.34 |
| Dapsone | −8.32 | 41.87 |
| 4,4'-methylene Bis(2,6-dimethylaniline) | −8.28 | 42.29 |
| 4,4'-ethylenedianiline | −8.08 | 43.23 |
| Diaminobenzophenone | −7.80 | 41.96 |
| 4,4'-diaminodiphenyl sulfide | −7.63 | 43.42 |
| 4,4'-methylene Bis(cyclohexyl amine) | −7.49 | 44.22 |
| Diaminodiphenyl methane | −7.45 | 41.90 |
| 4,4'-methylene Bis(N,N-dimethylaniline) | −7.35 | 39.50 |
| 4,4'-Oxydianiline | −7.00 | 42.41 |
| 4,4'-(hexafluoroisopropylidene)dianiline | −4.05 | 38.45 |
| Ethylenediindole | −10.88 | 44.58 |
| Thiodiindole | −10.42 | 43.87 |
| N,N'-diacetylthiodianiline | −9.32 | 43.47 |

TABLE 2

Computational inhibition constant based on ligand interaction with NMDAr NR2a subunit.

| Ligand | Inhibition Constant |
| --- | --- |
| 4,4'-methylene Bis(chloroaniline) | 517.15 nM |
| Dapsone | 793.94 nM |
| 4,4'-methylene Bis(2,6-dimethylaniline) | 845.46 nM |
| 4,4'-ethylenedianiline | 1.19 uM |
| Diaminobenzophenone | 1.92 uM |
| 4,4'-diaminodiphenyl sulfide | 2.54 uM |

TABLE 2-continued

Computational inhibition constant based on ligand interaction with NMDAr NR2a subunit.

| Ligand | Inhibition Constant |
| --- | --- |
| 4,4'-methylene Bis(cyclohexyl amine) | 3.25 uM |
| Diaminodiphenyl methane | 3.43 uM |
| 4,4'-methylene Bis(N,N-dimethylaniline) | 4.12 uM |
| 4,4'-Oxydianiline | 7.38 uM |
| 4,4'-(hexafluoroisopropylidene)dianiline | 1.07 mM |
| Ethylenediindole | 10.54 nM |
| Thiodiindole | 23.01 nM |
| N,N'-diacetylthiodianiline | 146.95 nM |

REFERENCES

1. Presynaptic NMDA receptors: Roles and rules. Bouvier, G.; Bidoret, C.; Casado, M.; Paoletti, P., Neuroscience (Amsterdam, Netherlands) (2015), 311, 322-340.
2. A structural biology perspective on NMDA receptor pharmacology and function. Regan, Michael C.; Romero-Hernandez, Annabel; Furukawa, Hiro. Current Opinion in Structural Biology (2015), 33, 68-75).
3. Synthesis of amorphous monomeric glass mixtures for organic electronic applications. Wu, You-Chi Mason; Molaire, Michel F.; Weiss, David S.; Angel, Felipe A.; DeBlase, Catherine R.; Fors, Brett P. Journal of Organic Chemistry (2015), 80(24), 12740-12745.
4. Bisindoles. 31. Acidic condensation of bisindoles with aromatic aldehydes and synthesis of new indole-containing polyamines. Ovsyannikov, N. N.; Samsoniya, Sh. A.; Suvorov, N. N.; Kogan, N. A. Khimiya Geterotsiklicheskikh Soedinenii (1993), (4), 476-80).
5. Synthesis of a novel methylene-bridged bis[carbazole] derivative and evaluation of its DNA and nucleotide binding properties. Li, Gang; Zhou, Xue; Yang, Peng; Jian, Yong; Deng, Tuo; Shen, Hongyan; Bao, Ying. Tetrahedron Letters (2014), 55(51), 7054-7059.
6. The novel cyclopropapyrroloindole(CPI) bisalkylators bearing methoxycarbonyl and trifluoromethyl groups. Fukuda Y, Furuta H, Kusama Y, Ebisu H, Oomori Y, Terashima S. Bioorg Med Chem Lett. 1998 Jun. 2; 8(11):1387-90.
7. Bacterial synthesis of unusual sulfonamide and sulfone antibiotics by flavoenzyme-mediated sulfur dioxide capture. Baunach, Martin; Ding, Ling; Willing, Karsten; Hertweck, Christian. Angewandte Chemie, International Edition (2015), 54(45), 13279-13283.
8. Synthesis of diaryl sulfones. VIII. In vitro growth-inhibiting action of diaryl sulfones. Yakugaku Zasshi (1961), 81, 1812-16.
9. Derivatives of bis(5-indolyl)methane and bis(5-indolyl) oxide: synthesis and antimicrobial properties. Samsoniya, Sh. A.; Lomtatidze, Z. Sh.; Ovsyannikova, N. N.; Suvorov, N. N. Khimiko-Farmatsevticheskii Zhurnal (1987), 21(7), 827-9.
10. Epiminocyclohepta[b]indole analogs as 5-HT6 antagonists. Henderson, Alan J.; Guzzo, Peter R.; Ghosh, Animesh; Kaur, Jagjit; Koo, Jia-Man; Nacro, Kassoum; Panduga, Shailaja; Pathak, Rashmi; Shimpukade, Bharat; Tan, Valentina; et al. Bioorganic & Medicinal Chemistry Letters (2012), 22(4), 1494-1498.
11. QSAR rationales for the 5-HT6 antagonistic activity of epiminocyclohepta[b]indoles. Choudhary, Manju; Sharma, Brij Kishore. Pharma Chemica (2014), 6(6), 321-330.
12. A novel NMDA receptor positive allosteric modulator that acts via the transmembrane domain. Wang T M, Brown B M, Deng L, Sellers B D, Lupardus P J, Wallweber H J A, Gustafson A, Wong E, Volgraf M, Schwarz J B, Hackos D H, Hanson J E, Neurobiol Dis. 2017 Apr. 29; 104:41-49.
13. N-methyl D-aspartate (NMDA) receptor antagonists and memantine treatment for Alzheimer's disease, vascular dementia and Parkinson's disease. Olivares D, Deshpande V K, Shi Y, Lahiri D K, Greig N H, Rogers J T, Huang X. Neuropharmacology (2017)S0028-3908 (17)30191-0.
14. Simultaneous triple therapy for the treatment of status epilepticus. Niquet J, Baldwin R, Norman K, Suchomelova L, Lumley L, Wasterlain C G. Neurobiol Dis. (2017) 104:41-49.
15. Ketamine reduces muscle pain, temporal summation, and referred pain in fibromyalgia patients. Graven-Nielsen, T.; Aspegren Kendall, S.; Henriksson, K. G.; Bengtsson, M.; Sorensen, J.; Johnson, A.; Gerdle, B.; Arendt-Nielsen, L. Pain (2000), 85(3), 483-491.
16. Potentiation of spinal N-methyl-D-aspartate-mediated nociceptive transmission by cocaine-regulated and amphetamine-regulated transcript peptide in rats. Endogenous Opioids Released During Non-Nociceptive Environmental Stress Induce Latent Pain Sensitization Via a NMDA-Dependent Process. Le Roy, Chloe; Laboureyras, Emilie; Gavello-Baudy, Stephanie; Chateauraynaud, Jeremy; Laulin, Jean-Paul; Simonnet, Guy. Journal of Pain (2011), 12(10), 1069-1079.
17. Altered excitatory-inhibitory balance in the NMDA-hypofunction model of Schizophrenia. Kehrer, Colin; Maziashvili, Nino; Dugladze, Tamar; Gloveli, Tengis. Frontiers in Molecular Neuroscience (2008), 1:6.
18. Agmatine rescues autistic behaviors in the valproic acid-induced animal model of autism. Kim, Ji-Woon; Seung, Hana; Kim, Ki Chan; Gonzales, Edson Luck T.; et al. Neuropharmacology (2017), 113(Part_A), 71-8.
19. NMDA antagonist treatment of depression. Williams, Nolan R.; Schatzberg, Alan F. Current Opinion in Neurobiology (2016), 36, 112-117.
20. Ketamine: translating mechanistic discoveries into the next generation of glutamate modulators for mood disorders. Zarate, C. A.; Machado-Vieira, R. Molecular Psychiatry (2017), 22(3), 324-327.
21. Characterization of NMDA induced depression in rat hippocampus: involvement of AMPA and NMDA receptors. Li, Rui; Dozmorov, Mikhail; Hellberg, Fredrik; Tian, Ye; Jilderos, Barbro; Wigstrom, Holger. Neuroscience Letters (2004), 357(2), 87-90.
22. Rapid and sustained antidepressant properties of an NMDA antagonist/monoamine reuptake inhibitor identified via transporter-based virtual screening. Talbot, Jeffery N.; Geffert, Laura M.; Jorvig, Jessica E.; Goldstein, Ruben I.; Nielsen, Cienna L.; Wolters, Nicholas E.; Amos, Mary Ellen; Munro, Caitlin A.; Dallman, Elizabeth; Mereu, Maddalena; et al. Pharmacology, Biochemistry and Behavior (2016), 150-151, 22-30
23. Shapiro, G. Preparation of pyrrolopyrimidine derivatives as NR2B NMDA receptor antagonists, U.S. Pat. No. 9,567,341, WO 20166044323.
24. Burch, R. Methods of treating depression using NMDA modulators such as GLYX-13. PCT Int. Appl. (2016), WO 2016025721 A1 20160218.
25. Schindler, R. et al. Pyrazoles as NMDA NR2B receptor inhibitors and their preparation. PCT Int. Appl. (2016), WO 2016025918 A1 20160218.

26. Kemp, J A, Tasker, T. Methods for treating disorders using NMDA NR2B-subtype selective antagonist. PCT Int. Appl. (2009), WO 2009118187 A1 20091001.
27. Gordon, E. Method for formulating combination medications for AHDH comprising dopaminergic and cholinesterase agents, and NMDA receptor antagonists, mGluR agonists, AMPA receptor antagonists and modulators. PCT Int. Appl. (2008), WO 2008083442 A1 20080717.
28. Goodman, L. S., A. Gilman, Brunton, L. L., Chabner, B. A., Knollmann, B. C. Goodman & Gilman's the Pharmacological Basis of Therapeutics. 12th/ed. 2011, New York: McGraw-Hill, Inc. Chapter XXI.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A compound having a structural formula as follows:

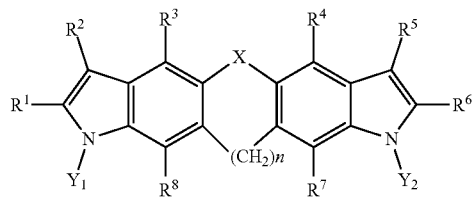

where, X is selected from the group consisting of —O—, —S—, —N(H)—, —Se—, —Si—, —CH$_2$—CH$_2$—, —CH$_2$—CH$_2$—CH$_2$—, —CH$_2$—CH$_2$—CH$_2$—CH$_2$—, (cis)-CH═CH—, (trans)-CH═CH—, —CH═CH—CH$_2$—, —CH$_2$—CH═CH—, —N═N—, —C(S)—, —N(H)S(O)—, —N(H)SO$_2$—, —N(H)O—, —N(H)S—, —S(O)—, —SO$_2$—, —PO$_4$—, —C(O)—, —CH$_2$—, —CF$_2$—, —C(CH$_3$)$_2$—, and a covalent bond;

Y$_1$ and Y$_2$ are each independently selected from the group consisting of hydrogen, deuterium, and tritium;

n is an integer from 1 to 6; and

R$^1$, R$^2$, R$^3$, R$^4$, R$^5$, R$^6$, R$^7$, and R$^8$ are each independently selected from the group consisting of hydrogen, hydroxyl, carboxyl, amino, aminoalkyl, nitro, hydroxymethyl, hydroxyalkyl, acetate, propionate, butyrate, thiol, thioalkyl, nitrile, a halogen, trifluoromethyl, methoxy, ethoxy, phenyl, guanidino, amidino, amide, alkylamide, sulfate, phosphate, imidazole, thiazole, a substituted or unsubstituted C$_{1-10}$ alkyl, a substituted or unsubstituted branched C$_{3-10}$ alkyl, a substituted or unsubstituted C$_{3-10}$ cycloalkyl, a substituted or unsubstituted arylalkyl, and a covalent bond.

2. The compound of claim 1, comprising a thiodiindole.
3. The compound of claim 1, comprising an ethylenediindole.
4. The compound of claim 1, wherein the compound effectively inhibits a function of a N-methyl-D-aspartate receptor (NMDAR) in an animal.
5. The compound of claim 4, wherein the animal is *Homo sapiens*.
6. The compound of claim 4, wherein the compound binds at least one of NMDAR's subunit isoforms, the NR2A and NR2B subunits.
7. A pharmaceutical composition, comprising a compound having a structural formula as follows:

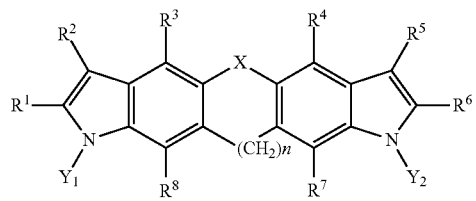

where, X is selected from the group consisting of —O—, —S—, —N(H)—, —Se—, —Si—, —CH$_2$—CH$_2$—, —CH$_2$—CH$_2$—CH$_2$—, —CH$_2$—CH$_2$—CH$_2$—CH$_2$—, (cis)-CH═CH—, (trans)-CH═CH—, —CH═CH—CH$_2$—, —CH$_2$—CH═CH—, —N═N—, —N═CH—, —CH═N—, —C(S)—, —N(H)S(O)—, —N(H)SO$_2$—, —N(H)O—, —N(H)S—, —S(O)—, —SO$_2$—, —PO$_4$—, —C(O)—, —CH$_2$—, —CF$_2$—, —C(CH$_3$)$_2$—, and a covalent bond;

Y$_1$ and Y$_2$ are each independently selected from the group consisting of hydrogen, deuterium, and tritium;

n is an integer from 1 to 6; and

R$^1$, R$^2$, R$^3$, R$^4$, R$^5$, R$^6$, R$^7$, and R$^8$ are each independently selected from the group consisting of hydrogen, hydroxyl, carboxyl, amino, aminoalkyl, nitro, hydroxymethyl, hydroxyalkyl, acetate, propionate, butyrate, thiol, thioalkyl, nitrile, a halogen, trifluoromethyl, methoxy, ethoxy, phenyl, guanidino, amidino, amide, alkylamide, sulfate, phosphate, imidazole, thiazole, a substituted or unsubstituted C$_{1-10}$ alkyl, a substituted or unsubstituted branched C$_{3-10}$ alkyl, a substituted or unsubstituted C$_{3-10}$ cycloalkyl, a substituted or unsubstituted arylalkyl, and a covalent bond;

and a pharmaceutically acceptable excipient, carrier, or diluent.

8. The pharmaceutical composition of claim 7, comprising a thiodiindole.
9. The pharmaceutical composition of claim 7, comprising an ethylenediindole.
10. The pharmaceutical composition of claim 7, wherein the compound effectively inhibits a function of a N-methyl-D-aspartate receptor (NMDAR) in an animal.
11. The pharmaceutical composition of claim 10, wherein the compound binds at least one of NMDAR's subunit isoforms, the NR2A and NR2B subunits.
12. The pharmaceutical composition of claim 7, formulated for use in humans.

* * * * *